(12) United States Patent
Moesli et al.

(10) Patent No.: US 7,641,636 B2
(45) Date of Patent: Jan. 5, 2010

(54) SYRINGE WITH A CLOSURE

(75) Inventors: Thomas Moesli, St. Gallen (CH); Peter Wolbring, St. Wendel (DE)

(73) Assignee: Schott AG, Mainz (DE)

( * ) Notice: Subject to any disclaimer, the term of this patent is extended or adjusted under 35 U.S.C. 154(b) by 351 days.

(21) Appl. No.: 11/604,506

(22) Filed: Nov. 27, 2006

(65) Prior Publication Data
US 2007/0156100 A1  Jul. 5, 2007

(30) Foreign Application Priority Data
Nov. 30, 2005  (DE) .................. 10 2005 058 133

(51) Int. Cl.
*A61M 5/32* (2006.01)
*A61M 5/178* (2006.01)
(52) U.S. Cl. .................. 604/198; 604/162; 604/164.08
(58) Field of Classification Search ......... 604/197–198, 604/162, 164.08
See application file for complete search history.

(56) References Cited
U.S. PATENT DOCUMENTS

| | | | |
|---|---|---|---|
| 2,671,449 A | 3/1954 | Dann | |
| 4,091,811 A | 5/1978 | Bates et al. | |
| 4,474,734 A | 10/1984 | Cooper | |
| 5,098,400 A * | 3/1992 | Crouse et al. | 604/192 |
| 5,336,200 A * | 8/1994 | Streck et al. | 604/198 |
| 5,584,817 A * | 12/1996 | van den Haak | 604/195 |
| 5,980,495 A | 11/1999 | Heinz et al. | |
| 6,719,732 B2 | 4/2004 | Courteix | |
| 2005/0027259 A1 * | 2/2005 | Vetter et al. | 604/192 |
| 2005/0038391 A1 | 2/2005 | Wittland et al. | |

FOREIGN PATENT DOCUMENTS

| | | |
|---|---|---|
| EP | 0 873 758 B1 | 10/1998 |
| FR | 2370482 | 6/1978 |
| WO | WO 93/10840 | 6/1993 |
| WO | WO 2004/071560 | 8/2004 |

* cited by examiner

Primary Examiner—Nicholas D Lucchesi
Assistant Examiner—Rebecca E Eisenberg
(74) Attorney, Agent, or Firm—Harness, Dickey & Pierce, P.L.C.

(57) ABSTRACT

A syringe with a closure is disclosed. The syringe comprises a needle projecting from a syringe body, the tip of the needle being enclosed by a closure cap when the syringe is in a closed position. A sealing element is provided for sealing the needle in the closed position. The sealing element has an annular, elastically deformable portion that can be sealingly pressed against the outer surface of the needle by means of the closure cap.

26 Claims, 2 Drawing Sheets

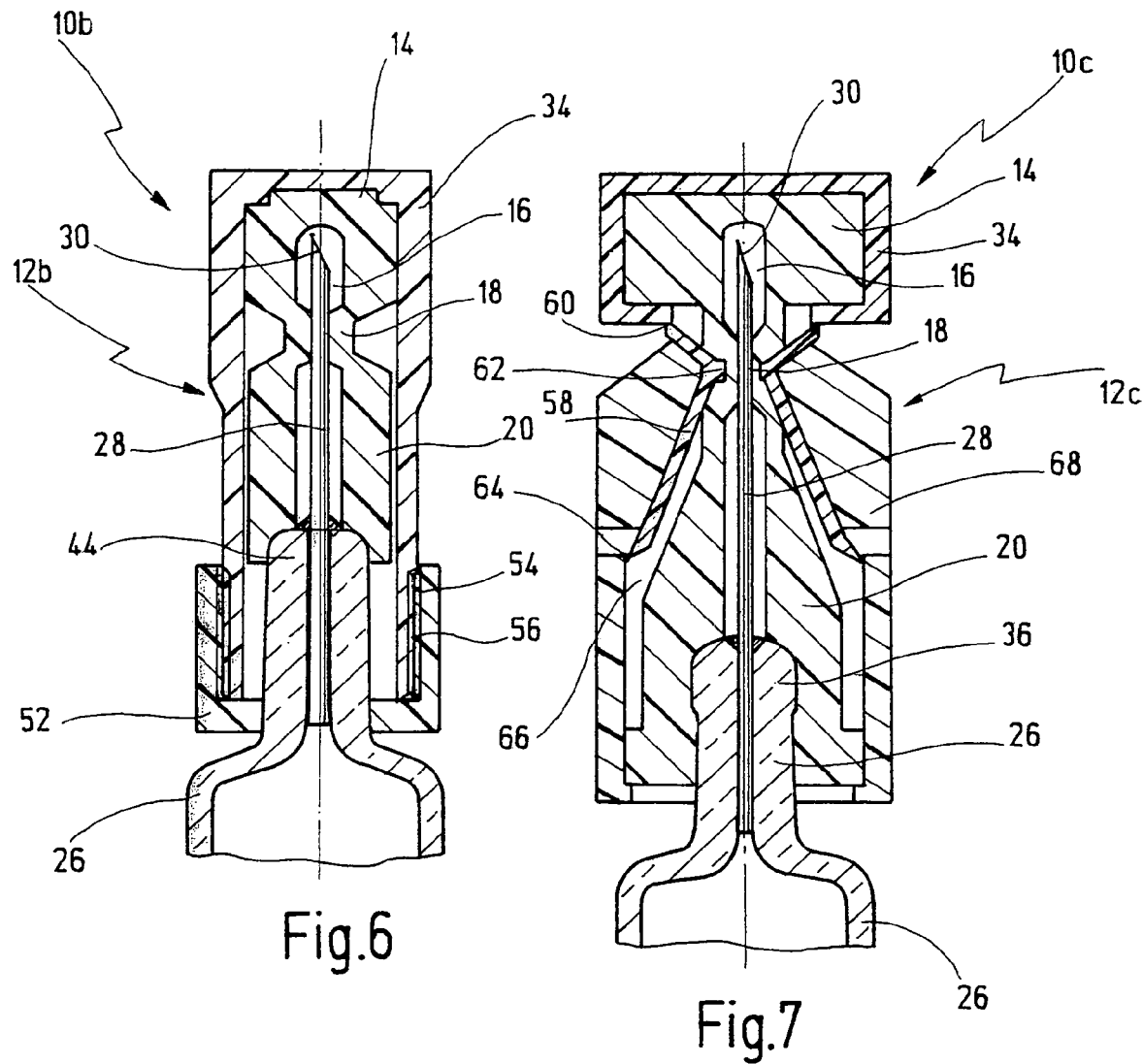

SYRINGE WITH A CLOSURE

BACKGROUND OF THE INVENTION

The invention relates to a syringe with a closure, comprising a needle projecting from a syringe body, the tip of said needle being enclosed by a closure cap when the syringe is in a closed position, and further comprising a sealing element for sealing the syringe in the closed position.

The invention also relates to a closure for a syringe having a needle projecting from a syringe body, said closure being configured for mounting on one end of said syringe body and having a closure cap that encloses a tip of said needle in a closed position, and further comprising a sealing element for sealing the needle in the closed position.

Such a syringe with such a closure is known, for example, from EP 0 873 758 B1.

The latter relates to a single-use syringe comprising an injector needle fixedly accommodated in the syringe body and further comprising a needle cap for protecting the injector needle. In order to provide a reliable seal for the prefilled syringe, the injector needle is inserted into a sealing element that is enclosed by the needle cap.

Similar syringes are known from U.S. Pat. No. 6,719,732 B2 and from US 2005/0038391 A1.

The syringes known from the prior art are filled with fluid substances and closed with a cap that is mostly referred to internationally as a "needle shield". The latter generally consists of a rubbery elastic material, mostly a synthetic rubber filled with mineral and with a Shore hardness between 40 A and 60 A. In order to make these needle shields mechanically more stable, they are often integrated into a rigid casing. Such an embodiment is then referred to as a "rigid needle shield". Syringes and closures of the kind initially specified basically perform two essential functions. On the one hand, they cover the tip of the needle inserted into the syringe body, while on the other hand they distally seal the interior of the syringe body in a fluid-tight manner. This occurs in a simple manner by inserting the tip of the needle into the soft material of the protective cap.

This kind of seal involves considerable disadvantages for the syringe and ultimately for the patients who are treated with this syringe. Thin-walled needles with small outer diameters, in particular, such as those mostly used nowadays for prefilled syringes, have a bevel that is mechanically highly sensitive. The more filigree the needle, the more prone the bevel is to damage. A needle that has been inserted once into any medium may already have lost some of its sharpness. In some cases, the tip of the needle may be deformed into a shape like a crocheting needle even when inserted into very soft media. However, using needles that do not have optimal sharpness and are deformed at the tip leads causes patients a considerable increase in pain on puncture. There is also the risk of bleeding, hematomas or even abscesses being caused by deformed bevels on needles. Furthermore, it has long been known that, when needles are inserted into rubbery elastic materials, particles are punched out that in the worst case can clog the needle and prevent injection of the drug. If, in contrast, the particles remain mobile, it is possible that they will be flushed into the patient on injection.

SUMMARY OF THE INVENTION

It is a first object of the present invention is to disclose a syringe and a closure for a syringe, with which a prefilled syringe can be reliably sealed without the tip of the needle being inserted into a sealing material.

It is a second object of the present invention to disclose a syringe that can be used as a prefilled syringe without any risk of contamination or damage to the needle thereof.

It is a third object of the present invention to disclose a syringe that can be used as a prefilled syringe, is easy to manufacture and reliable.

These and other objects of the invention are achieved by providing a syringe with a sealing element having an annular, elastically deformable portion that can be sealingly pressed against the outer surface of the needle by means of the closure cap.

The object of the invention is further accomplished in a closure of the kind initially specified, by the sealing element having an annular, elastically deformable portion that can be sealingly pressed against the outer surface of the needle by means of the closure cap.

The problem of the invention is completely solved in this manner.

The invention avoids any insertion of the tip of the needle into a sealing element. Instead, the needle is sealed at the distal end in a fluid-tight manner by it being possible to sealingly press the annular, elastically deformable portion against the outer surface of the needle in the closed position. In this way, the disadvantages of the prior art solutions can be avoided. In particular, it is possible to avoid any contact at all between the tip of the needle and the sealing material. This means that the tip cannot become deformed. A punch-out effect is likewise avoided, so no foreign matter punched out by insertion of the needle into a sealing material can result in contamination.

In one advantageous development of the invention, the sealing element includes a cavity in which the tip of the needle is accommodated, preferably contactlessly, in the closed position.

This further reduces the risk of potential contamination of the syringe in the tip region of the needle.

According to another configuration of the invention, the sealing element comprises a head part or element that is connected via the annular portion to a pressure part or element, wherein said annular portion can be pressed against the outer surface of the needle by a relative movement between the head element and the pressure element.

It is possible in this way to ensure that the syringe is cleanly sealed after a filling operation, in that after completion of the syringe filling operation, the head element and the pressure element are moved relative to each other in order to press the annular portion against the outer surface of the needle.

According to another configuration of the invention, at least the head element is at least partially enclosed by the closure cap and can be moved relative to the pressure element by means of the closure cap.

Moving the closure cap relative to the pressure element can therefore cause the head element to be moved by the closure cap in order to seal the annular portion.

According to another configuration of the invention, the head element and the pressure element are axially movable towards each other.

In addition, or alternatively, the head element and the pressure element can be twisted relative to each other.

By means of axial movement or a rotational movement between the head element and the pressure element, it is therefore possible for the annular portion to be pressed against the outer surface of the needle.

According to another configuration of the invention, the closure cap can be snap-locked into position in the closed position.

This is a particularly simple way of securing the closure cap in the against unintentional opening when the syringe has been filled.

According to another configuration of the invention, a bead is provided at the distal end of the syringe body, to which bead the closure cap or the pressure element is affixed in the closed position.

This enables simple fastening of the closure cap to the syringe body.

According to yet another configuration of the invention, the closure cap can be fixed to the syringe body by means of a screw thread, preferably by means of a Luer lock thread.

This is another way in which the closure cap can be locked in the closed position in a simple manner.

According to another configuration of the invention, an indicator element is provided that indicates a first-ever movement of the closure cap out of the closed position.

In this way, a first-ever movement of the syringe can be made visually distinguishable, in order to ensure that only such syringes are used in which the closure cap is still in the closed position with the original filling.

According to another configuration of the invention, the closure cap has a snap-fit connection with clip elements that press the annular portion against the outer surface of the needle in the closed position.

In this way, sealing of the needle is further enhanced.

In an additional development of this configuration, the snap-fit connection is embodied as one that cannot be non-destructively released, in which a first-ever movement of the closure cap out of the closed position is visually distinguishable.

In this way, visual indication of a first-ever movement of the closure cap out of the closed position can be realized by simple means.

According to another configuration of the invention, the head element and the pressure element consist of the same material and are of integral construction.

In this way, the diameter in the annual portion can be reduced in order to seal the needle at its outer surface, in a particularly simple manner by means of a relative movement between the sealing element and the pressure element.

It is self-evident that the features of the invention as mentioned above and to be explained below can be applied not only in the combination specified in each case, but also in other combinations or in isolation, without departing from the scope of the invention.

BRIEF DESCRIPTION OF THE DRAWINGS

Additional features and advantages of the invention derive from the following description of preferred embodiments with reference to the drawings, in which

FIG. 6 shows a practical application of the insert shown in FIGS. 4 and 5, in a syringe made of glass and with a closure that can be snap-locked by rotation; and FIG. 7 shows a further modification of a syringe according to the invention, comprising a closure that can be snap-locked in a closed position, said closure comprising a snap-fit connection that is destroyed when released from the closed position, thus serving as an indicator element for first-ever opening of the closure.

DETAILED DESCRIPTION OF THE PREFERRED EMBODIMENTS

Figure 1:
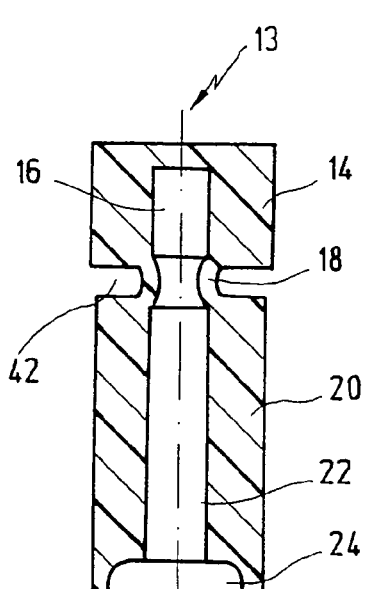
FIG. 1 shows a longitudinal cross-section of an insert or sealing, comprising a head element and a pressure element that can be used in a closure according to the invention.

FIG. 1 shows, in a longitudinal cross-sectional view, an insert or sealing 13 with reference to which one possible principle of the inventive closure shall firstly be described.

Insert or sealing 13 consists of a rubbery elastic material and includes a head part or element 14 and a pressure part or element 20 that are interconnected via an annular, elastically deformable portion 18 with a gap being formed therebetween. Head part 14 is cylindrical in shape and contains a cylindrical cavity 16 that continues in a matching cylindrical cavity 22 of the same diameter inside pressure part 20. The annular, elastically deformable portion 18 defines a tapering of said diameter between the two cavities 16, 22. Pressure part 20 has a somewhat smaller outer diameter than head part 14 and ends at its bottom end in a recess 24 of greater diameter than cavity 22. Pressure part 20 can be placed by means of recess 24 onto the distal end of a syringe body.

"Distal" in this application is understood to mean the side of the syringe that faces the patient and away from the user.

Such an insert 13 can now be used to seal the needle of a syringe filled with a fluid. All that is needed to do this is to perform a relative movement between head part 14 and pressure part 20, either by an axial displacement or by twisting these two elements, whereupon the inner diameter of the annular portion 18 decreases and the size of gap 42 between head part 14 and pressure part 20 simultaneously becomes smaller. Due to a corresponding reduction in the inner diameter of annular portion 18, the latter engages the outer surface of a needle of the syringe and can seal it in a fluid-tight manner.

In this way, a glass or plastic syringe filled with a pharmaceutical product can be reliably sealed on the distal side so that the fluid contained therein cannot leak out, not even after several years in storage.

To this end, it is expedient when the outer diameter of head element 14 is somewhat larger than the outer diameter of pressure element 20 to facilitate manipulation of head element 14 by means of a closure cap of the closure, in order to bring about the desired reduction in diameter.

Figure 2:
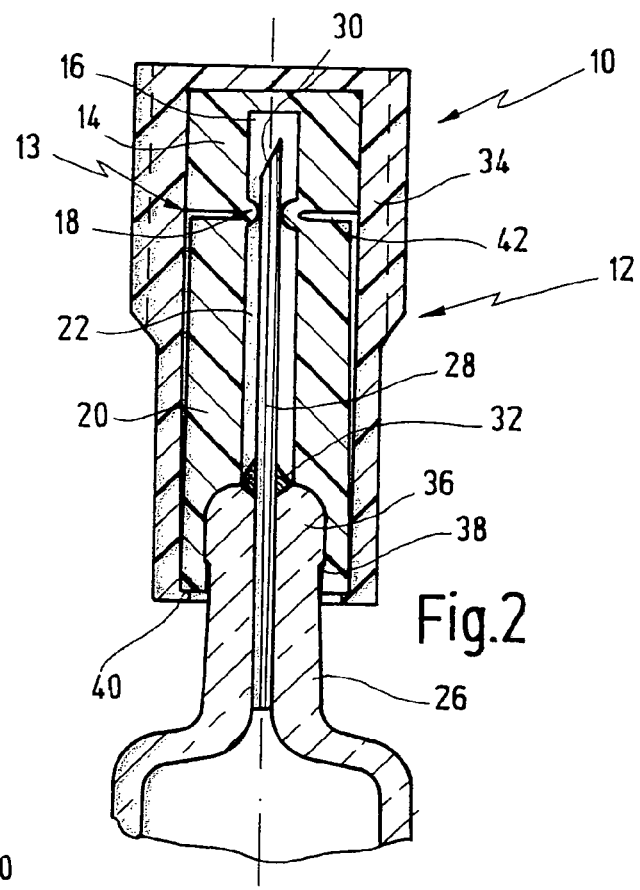
FIG. 2 shows, in a longitudinal cross-sectional view, a practical application of the insert shown in FIG. 1, in a first embodiment of a closure according to the invention, for a glass syringe with a needle adhesively inserted therein.

A first possible practical embodiment of a syringe according to the invention is shown in FIG. 2, where it is labeled in its entirety with reference numeral 10.

Syringe 10 comprises a glass syringe body 26, into the distal end of which a needle 28 is glued with an adhesive 32. A closure 12, labeled in its entirety with reference numeral 12, is used to seal syringe 10 at its distal end and to protect needle 28. Closure 12 includes an insert or sealing 13 of the kind described previously with reference to FIG. 1, comprising a head element 14 and a pressure element 20. Pressure element 20 is provided on its side facing syringe body 26 with a suitable recess so that pressure element 20 can be placed and snap-locked onto a matching bead 36 on the end of syringe body 26. A protrusion 38 that engages bead 36 is used for snap-locking.

Insert or sealing 13 is enclosed by a closure cap 34, by means of which head element 14 is displaced a little in the direction of pressure element 20. In the closed position shown in FIG. 2, closure cap 34 thus engages, with a radially inwardly projecting protrusion 40, the proximal end of pressure element 20 and snap-locks onto it. In this way, closure 12 can be securely snap-locked in the closed position onto bead 36 of syringe body 26.

Due to the axial displacement of head element 14 in the direction of pressure element 20, the gap 42 between head element 14 and pressure element 20 is significantly reduced in size in comparison to the view in FIG. 1, with the result that the annular, elastically deformable portion 18 sealingly engages the outer surface of needle 28. A fluid-tight seal of needle 28 is thus effected just behind tip 30 of needle 28 by means of annular portion 18, with the result that no fluid is able to leak out of the lumen of the syringe and needle 28.

Tip 30 of needle 28 is accommodated contactlessly in cavity 16 of head element 14, thus reliably avoiding any damage to tip 30 or any contamination due to insertion into the material of sealing element 14. To use syringe 10, closure cap 34 needs only to be pulled outwards and removed from the snap-locked position. During this pull-off movement, head element 14 is moved outwards, as a result of which gap 42 between head element 14 and pressure element 20 increases in size and closure 12 can be pulled off easily from needle 28.

Figure 3:
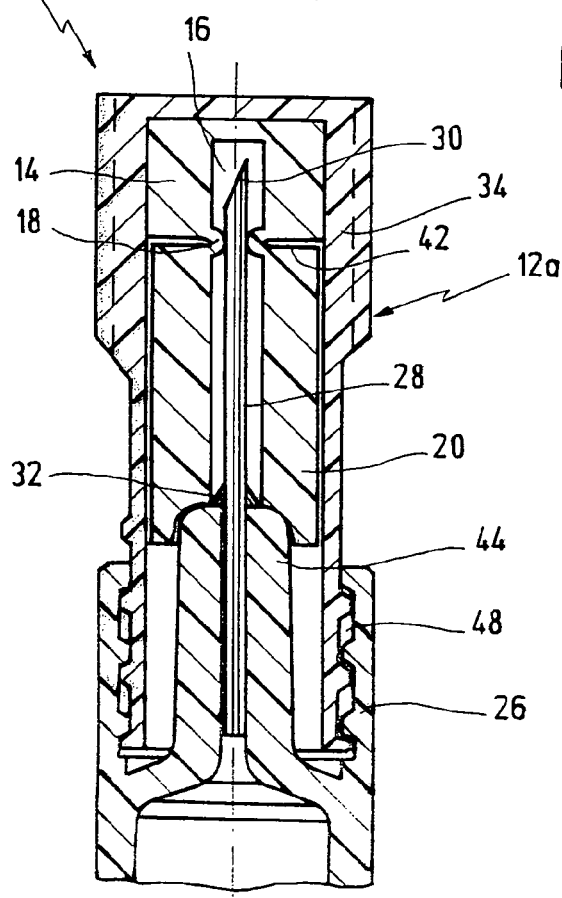
FIG. 3 shows a modified variant of the embodiment shown in FIG. 2, configured as a plastic syringe in which the closure cap is screwed into a Luer lock thread.

A modified variant of the embodiment in FIG. 2 is shown in FIG. 3, where it is labeled in its entirety with reference numeral 10a.

Here, and in the embodiments that follow, corresponding reference numerals are used for corresponding parts.

Syringe 10a is a plastic syringe in which closure cap 34 is screwed into the distal end of syringe body 26 by means of a Luer lock thread 48. Needle 28 is glued into a matching recess at the distal end 44 of syringe body 26 using an adhesive 32. By twisting closure cap 34, head element 14 of closure 12a can be moved in the axial direction towards pressure element 20 in order to narrow gap 42 between head element 14 and pressure element 20, as described previously with reference to FIG. 2.

As in the embodiment according to FIG. 2, the inner diameter of annular portion 18 is thus reduced, with the result that said annular portion sealingly engages the outer surface of needle 28 just behind tip 30 thereof and seals it in a fluid-tight manner, in the closed position shown in FIG. 3. Closure 12a can be easily released by unscrewing the Luer lock out of the closed position, so that closure cap 34 can be removed for the syringe to be used.

Figure 5:
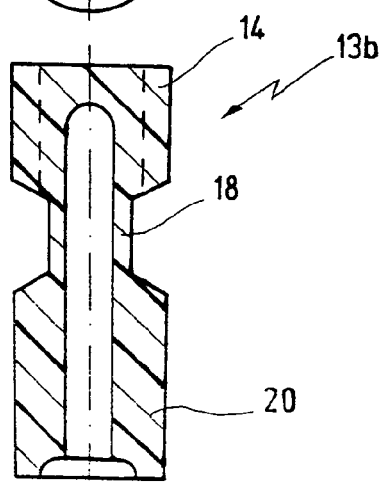
FIG. 5 shows a plan view of the insert shown in FIG. 4.
Figure 4:
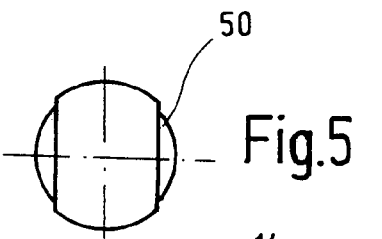
FIG. 4 shows, in longitudinal cross-section, a modified variant of the insert or sealing shown in FIG. 1, wherein the head element and the pressure element can be twisted relative to each other.

Another variant of the closure according to the invention shall now be described in more detail with reference to FIGS. 4-6. The closure again comprises an insert or sealing 13b, consisting of a head part or element 14 and a pressure part or element 20 that are interconnected via an annular, elastically deformable portion 18.

Unlike the embodiments described previously, a reduction in the diameter of annular portion 18 is achieved in this case by twisting, not by compressing. Twisting head element 14 and pressure element 20 relative to each other causes a reduction in the diameter of annular portion 18, in order to seal a previously inserted needle in this region. As can be seen from FIG. 5, head element 14 can have flattened areas 50, for example on its two outer surfaces, to enable simple twisting of sealing element 14 with the aid of a closure cap placed over it.

Such an embodiment of such a syringe with such a closure is shown in FIG. 6, where it is labeled in its entirety with reference numeral 10b. Syringe 10b includes a closure 12b comprising a closure cap 34 by means of which head element 14 can be twisted relative to pressure element 20. This leads to a reduction in the diameter of annular portion 18, by means of which head element 14 and pressure element 20 are interconnected. In this manner, needle 28 is sealed, likewise near its tip 30, by annular portion 18. In the closed position as shown in FIG. 6, closure cap 34 is snap-locked by means of suitable snap-lock elements 56 onto associated snap-lock elements 54 of a fastening element 52 held on the distal end 44 of syringe body 26. The closure cap can be secured against being pulled off by means of frictional engagement, in the simplest case, or by means of additional snap-lock elements (not shown).

Another embodiment of a syringe 10c according to the invention, comprising a closure 12c according to the invention, is shown in FIG. 7.

In this case, closure 12c includes a head element or part 14 and a pressure element or part 20 that are interconnected via an elastically deformable, annular portion 18. Pressure element 20 is placed at its proximal end onto a bead 36 of syringe body 26 and locked onto the latter. A cap member 68 is pushed onto the pressure element from the outside and snap-locked onto the proximal end of pressure element 20.

Closure cap 34 encloses head element 14 on the outside thereof and includes two hinged clip elements 58 at its proximal end that are connected on either side via integral hinges 60 to closure cap 34 and can be pivoted relative to the latter. Said hinged clip elements 58 pass through matching recesses in the cap member 68 and their ends 64 snap into place in associated slots 66 in cap member 68. In the closed position shown in FIG. 7, hinged clip elements 58 externally engage matching protrusions 62 in annular portion 18, and press said portion onto the outer surface of needle 28.

In the closed position shown in FIG. 7, closure cap 34 is snap-locked with ends 64 in slots 66 in such a manner that releasing the lock by pulling off closure cap 34 is possible only by destroying hinged clip elements 58, which is visually distinguishable.

In this way, an originality closure is assured, in that first-ever removal of closure cap 34 from the closed position leads to destruction of hinged clip elements 58 in a region of their ends 64.

What is claimed is:

1. A syringe comprising:
    a syringe body;
    a needle projecting from said syringe body;
    a closure cap arranged on said syringe body and being movable between a closed position in which the closure cap encloses a tip of said needle and between a released position in which the closure cap can be removed from said syringe body exposing the tip of said needle;
    a sealing held within said closure cap and enclosing the tip of said needle when in said closed position, said sealing comprising a head part and a pressure part, both being connected by an annular, elastically deformable portion defined by an annular gap between said pressure part and said head part;
    wherein said closure cap is configured for engaging said syringe body and said head part and for pressing said head part against said pressure part when in said closed position, thereby urging said elastically deformable portion inwardly against an outer surface of said needle to sealingly engage around the outer surface thereof.

2. The syringe of claim 1, wherein said head part of said sealing further comprises a cavity wherein said tip of said needle is contactlessly accommodated in the closed position.

3. The syringe of claim 1, wherein said head part and said pressure part of said sealing are configured axially movable towards each other.

4. The syringe of claim 1, wherein said head part and said pressure part of said sealing are configured twistable relative to each other.

5. The syringe of claim 1, wherein said closure cap lockingly engages said syringe body in said closed position.

6. The syringe of claim 5, wherein said syringe body further comprises a bead provided at a distal end of said syringe body, to which bead said closure cap is affixed in said closed position.

7. The syringe of claim 1, wherein said syringe body and said closure cap further comprise screw threads for screw attachment of said closure cap to said syringe body in said closed position.

8. The syringe of claim 5, wherein said closure cap further comprises a snap-fit connection connecting said closure cap with said syringe body in said closed position, said snap-fit connection comprising clip elements configured for pressing said annular portion of said sealing against the outer surface of said needle in the closed position.

9. The syringe of claim 8, wherein said snap-fit connection is configured as irrevocably releasable optically indicating a first-ever movement of said closure cap out of the closed position.

10. The syringe of claim 1, wherein said head and pressure parts and said elastically deformable portion of said sealing element are integrally formed from an elastically deformable material.

11. A syringe comprising:
a syringe body;
a needle projecting from said syringe body;
a closure cap arranged on said syringe body and being movable between a closed position in which the closure cap encloses a tip of said needle and between a released position in which the closure cap can be removed from said syringe body exposing the tip of said needle;
a sealing held within said closure cap and enclosing the tip of said needle when in said closed position, said sealing comprising a head part and a pressure part, both being connected by an annular, elastically deformable portion defined by an annular gap between said pressure part and said head part; and
at least one indicator element arranged between said syringe body and said closure cap being configured irrevocably releasable for indicating a first-ever movement of the closure cap out of the closed position;
wherein said closure cap is configured for engaging said syringe body and said head part and for pressing said head part against said pressure part when in said closed position, thereby urging said elastically deformable portion inwardly against an outer surface of said needle to sealingly engage around the outer surface thereof.

12. The syringe of claim 11, wherein said closure cap further comprises a snap-fit connection connecting said closure cap with said syringe body in said closed position, said snap-fit connection comprising clip elements configured for pressing said annular portion of said sealing against the outer surface of said needle in the closed position.

13. A closure cap configured for attachment to a syringe body comprising a needle projecting from the syringe body, said closure cap comprising:
a sealing held within said closure cap and enclosing the tip of said needle when the closure cap is in a closed position, said sealing comprising a head part and a pressure part, both being connected by an annular, elastically deformable portion defined by an annular gap between said pressure part and said head part;
engaging means for engaging said syringe body when in said closed position, said closure cap pressing said head part against said pressure part when in said closed position, thereby urging said elastically deformable portion inwardly against an outer surface of said needle to sealingly engage around the outer surface thereof in said closed position;
said engaging means releasing said closure cap when moving said closure cap from said closed position into a released position for removing said closure cap from said syringe body thereby exposing said needle.

14. The closure of claim 13, wherein said head part of said sealing element comprises a cavity in which a tip of the needle is accommodated, contactlessly in the closed position.

15. The closure of claim 13, wherein said head part and said pressure part of said sealing element are axially movable towards each other when pressing said closure against said syringe body.

16. The closure of claim 13, wherein said head part and said pressure part of said sealing element can be twisted relative to each other by rotating said closure relative to said syringe body.

17. The closure of claim 13, wherein said closure cap further comprises snap means for snap-lockingly engaging said syringe body in the closed position.

18. The closure of claim 13, wherein said closure cap further comprises screw threads for screw engagement to screw threads provided on said syringe body.

19. The closure of claim 13, wherein said closure cap further comprises indicator means for indicating a first-ever movement of said closure cap out of the closed position.

20. The closure of claim 13, wherein said head and pressure parts and said elastically deformable portion of said sealing element are integrally formed from an elastically deformable material.

21. The syringe of claim 2, wherein each of said head part and said pressure part contain a cylindrical cavity whose diameter is greater than the diameter of the needle.

22. The syringe of claim 2, wherein the needle is engaged solely by said annular portion in said closed position.

23. The syringe of claim 11, wherein each of said head part and said pressure part contain a cylindrical cavity whose diameter is greater than the diameter of the needle.

24. The syringe of claim 11, wherein the needle is engaged solely by said annular portion in said closed position.

25. The closure of claim 14, wherein each of said head part and said pressure part contain a cylindrical cavity whose diameter is greater than the diameter of the needle.

26. The closure of claim 14, wherein the needle is engaged solely by said annular portion in said closed position.

* * * * *